US008440395B2

(12) United States Patent
Kerr et al.

(10) Patent No.: US 8,440,395 B2
(45) Date of Patent: May 14, 2013

(54) METHODS OF DETECTING AND TREATING COLON DISORDERS

(75) Inventors: William G. Kerr, Syracuse, NY (US); Joseph M. McKinley, Tampa, FL (US)

(73) Assignee: University of South Florida, Tampa, FL (US)

( * ) Notice: Subject to any disclaimer, the term of this patent is extended or adjusted under 35 U.S.C. 154(b) by 535 days.

(21) Appl. No.: 12/577,161

(22) Filed: Oct. 10, 2009

(65) Prior Publication Data

US 2010/0183521 A1 Jul. 22, 2010

Related U.S. Application Data

(63) Continuation-in-part of application No. 10/473,741, filed as application No. PCT/US02/10350 on Apr. 2, 2002, now Pat. No. 7,704,963.

(60) Provisional application No. 60/280,107, filed on Apr. 2, 2001, provisional application No. 61/104,496, filed on Oct. 10, 2008.

(51) Int. Cl.
*C12Q 1/68* (2006.01)
*C12P 19/34* (2006.01)
*G01N 33/567* (2006.01)
*C07H 21/02* (2006.01)
*C07H 21/04* (2006.01)

(52) U.S. Cl.
USPC ............. 435/6; 435/91.1; 436/503; 536/23.1; 536/24.3; 536/24.31

(58) Field of Classification Search ............. 435/6, 91.1, 435/91.2, 91.5; 536/23.1, 24.3, 24.31; 436/503
See application file for complete search history.

(56) References Cited

U.S. PATENT DOCUMENTS

| 7,704,963 | B2 | 4/2010 | Kerr et al. |
| 2004/0235765 | A1 | 11/2004 | Kerr et al. |
| 2009/0010908 | A1* | 1/2009 | Gow et al. ..................... 424/94.1 |
| 2010/0266548 | A1 | 10/2010 | Kerr et al. |
| 2010/0273671 | A1* | 10/2010 | Lauwerys et al. ................. 506/9 |
| 2011/0165566 | A1 | 7/2011 | Wittliff et al. |
| 2011/0257034 | A1* | 10/2011 | Barany et al. ..................... 506/9 |

FOREIGN PATENT DOCUMENTS

WO WO 02/078614 A3 10/2002

OTHER PUBLICATIONS de Jager et al., Genes & Immunity, vol. 8, pp. 387-397 (2007).*
Wang et al., J. Immunol, vol. 166, pp. 4586-4595 (2001).*
Kerr, W.G. et al. "Transcriptionally defective retroviruses containing lacZ for the in situ detection of endogenous genes and developmentally regulated chromatin" *Cold Spring Harbor Symposia on Quantitative Biology*, 1989, 54:767-776.
Agrawal, S. et al. "Antisense therapeutics: is it as simple as complementary base recognition" *Molecular Medicine Today*, Feb. 2000, 6:72-81.
Branch, A.D. "A good antisense molecule is hard to find" *Trends in Biochem Sci*, Feb. 1998, 23:45-50.
Chirila, T.V. et al. "The use of synthetic polymers for delivery of therapeutic antisense oligodeoxynucleotides" *Biomaterials*, 2002, 23:321-342.
Crooke, S.T. "Basic principles of antisense therapeutics" in Antisense Research and Application, Chapter 1, pp. 1-50, S. Crooke, Editor, Springer-Verlag, 1999.
Examination Report dated Dec. 28, 2006 in European Application No. 02731226.3, pp. cover page, 1-7.
Examination Report dated Dec. 18, 2007 in European Application No. 02731226.3, pp. cover page, 1-4.
Examination Report dated Dec. 8, 2008 in European Application No. 02731226.3, pp. cover page, 1-2.
Holen, T. et al. "Positional effects of short interfering RNAs targeting the human coagulation trigger Tissue Factor" *Nucleic Acids Research*, Apr. 15, 2002, 30(8):1757-1766.
Karim, M.A. et al. "Mutations in the Chediak-Higashi Syndrome Gene (CHS1) indicate requirement for the complete 3801 amino acid CHS protein" *Human Molecular Genetics*, 1997, 6(7):1087-1089.
Nagle, D.L. et al. "Identification and mutation analysis of the complete gene for Chediak-Higashi syndrom" *Nature Genetics*, Nov. 1996, 14:307-311.
Opalinska, J.B. et al."Nucleic-Acid Therapeutics: Basic Principles and Recent Applications" *Nature Reviews: Drug Discovery*, Jul. 2002, 1:503-514.
Peracchi, A. "Prospects for antiviral ribozymes and deoxyribozymes" *Reviews in Medical Virology*, 2004, 14:47-64.
Perou, C.M. et al. "The Beige/Chediak-Higashi Syndrome Gene Encodes a Widely Expressed Cytosolic Protein" *The Journal of Biological Chemistry*, Nov. 1997, 272(47):29790-29794.
Shiflett, S.L. et al. "Chediak-Higashi Syndrome: A Rare Disorder of Lysosomes and Lysosome Related Organelles" *Pigment Cell Res*, 2002, 15:251-257.
Spritz, R.A. "Genetic Defects in Chediak-Higashi Syndrome and the *beige* Mouse" *Journal of Clinical Immunology*, 1998, 18(2):97-105.
Wang, J.W. et al. Identification of a Novel Lipopolysaccharide-Inducible Gene with Key Features of Both a Kinase Anchor Proteins and chs1/beige Proteins, *The Journal of Immunology*, 2001, 166:4586-4595.
Wang, J.W. et al. "Identification of a novel LPS-inducible gene that involves in apoptosis and has key features of both protein kinase A anchor and chs1/beige genes" *FASEB Journal*, 2001, 15(5):A1175, abstract 918.5.
Wang, J.W. et al. "Inhibition of Apoptosis by the BEACH Domain and WD Repeats of Gene *Iba* That Has Key Features of Both Protein Kinase A Anchor and *chs1/beige* Genes" *The Scientific World Journal*, 2001, 1(Supp 3):96, 3 pages.

(Continued)

*Primary Examiner* — Jane Zara
(74) *Attorney, Agent, or Firm* — Saliwanchik, Lloyd & Eisenschenk

(57) ABSTRACT

The subject invention pertains to a method of detecting colon disorders including inflammatory bowel disease, such as Crohn's disease and ulcerative colitis, based on underexpression of Lipopolysaccharide Responsive Beige-like Anchor (LRBA). Advantageously, the invention may be used to test for inflammatory bowel disease using a blood sample from a subject before a more invasive test for colon disorders is employed. The invention also pertains to methods of treating a colon disorder in a subject in which the colon disorder is detected.

16 Claims, 6 Drawing Sheets

OTHER PUBLICATIONS

Webb, A. et al. "*BCL-2* antisense therapy in patients with non-Hodgkin lymphoma" *The Lancet*, Apr. 19, 1997, 349:1137-1141.

Abreu, M.T. et al. "Translational Research in Inflammatory Bowel Disease" *Mount Sinai Journal of Medicine*, Dec. 2006, 73(8):1067-1073.

Best, W.R. "Predicting the Chron's Disease Activity Index From the Harvey-Bradshaw Index" *Inflamm Bowel Dis*, Apr. 2006, 12(4):304-310.

Browning, B.L. et al. "Has Toll-Like Receptor 4 Been Premature Dismissed as an Inflammatory Bowel Disease Gene? Association Study Combined with Meta-Analysis Shows Strong Evidence for Association" *American Journal of Gastroenterology*, Nov. 2007, 102(11):2504-2512.

De Jager, P.L. et al. "The role of the Toll receptor pathway in susceptibility to inflammatory bowel diseases" *Genes and Immunity*, 2007, 8:387-397.

Fukata, M. et al. "Toll-Like Receptor-4 Promotes the Development of Colitis-Associated Colorectal Tumors" *Gastroenterology*, 2007, 133(6):1869-1881.

Fukata, M. et al. "TLR4 signalling in the intestine in health and disease" *Biochemical Society Transactions*, 2007, 35:1473-1478.

Genbank Accession No. AAG48558.2 (Nov. 5, 2001), pp. 1-3.
Genbank Accession No. AF216648 (Nov. 5, 2001), pp. 1-5.
Genbank Accession No. AF467287 (Aug. 7, 2002), pp. 1-5.
Genbank Accession No. BC064834.1 (Jan. 3, 2005), pp. 1-4.
Genbank Accession No. EAX04996 (Dec. 18, 2006), pp. 1-5.

Gribar, S.C. et al. "The role of epithelial Toll-like receptor signaling in the pathogenesis of intestinal inflammation" *Journal of Leukocyte Biology*, Mar. 2008, 83:493-498.

Hume, G.E. et al. "Novel *NOD2* Haplotype Strengthens the Association Between *TLR4* Asp299Gly and Crohn's Disease in an Australian Population" *Inflammatory Bowel Diseases*, 2008, 14(5):585-590.

Kaplan, J. et al. "Chediak-Higashi syndrome" *Current Opinion in Hematology*, 2008, 15:22-29.

Karrasch, T. et al. "Nf-κB and the Intestine: Friend or Foe?" *Inflamm Bowel Dis*, 2008, 14:114-124.

Kerr, W.G. et al. "Analysis of lipopolysaccharide-response genes in B-lineage cells demonstrates that they can have differentiation stage-restricted expression and contain SH2 domains" *Proc Natl Acad Sci USA*, Apr. 1996, 93:3947-3952.

Komarova, E.A. et al. "p53 is a suppressor of inflammatory response in mice" *The FASEB Journal*, Jun. 1, 2005, 19(8):1030-1032.

Narayan, S. et al. "Role of *APC* and DNA mismatch repair genes in the development of colorectal cancers" *Molecular Cancer*, Dec. 2003, 2:41, 15 pages.

Sandborn, W.J. et al. "MMX Multi Matrix System® mesalazine for the induction fo remission inpatients with mild-to-moderate ulcerative colitis: a combined analysis of two randomized, double-blind, placebo-controlled trials" *Alimentary Pharmacology & Therapeutics*, 2007, 26(2):205-215.

Shinzaki, S. et al. "IgG Oligosaccharide Alterations Are a Novel Diagnostic Marker for Disease Activity and the Clinical Course of Inflammatory Bowel Disease" *American Journal of Gastroenterology*, May 2008, 103(5):1173-1181.

Van Limbergen, J. et al. "The Genetics of Inflammatory Bowel Disease" *American Journal of Gastroenterology*, 2007, 102:2820-2831.

Wang, J.W. et al. "Deregulated expression of LRBA facilitates cancer cell growth" *Oncogene*, Apr. 2004, 23:4089-4097.

Wang, N. et al. "BEACH Family of Proteins: Phylogenetic and Functional Analysis of Six *Dictyostelium* BEACH Proteins" *Journal of Cellular Biochemistry*, 2002, 86:561-570.

McKinley, J. M. et al. May 2008. LRBA: A potential novel gene in the pathogenesis of inflammatory bowel disease. Poster presented at *Digestive Disease Week* in San Diego, California.

McKinley, J. M. et al. May 2009. LRBA: A Link Between Inflammation and carcinogenesis in the Gastrointestinal Tract. Poster presented at *Digestive Disease Week* in Chicago, Illinois.

* cited by examiner

| Disease | Age | Location | Duration | Sex | ANTI-TNF | Disease activity | LRBA (Quant) |
|---|---|---|---|---|---|---|---|
| UC | 34 | Pancolitis | 1 | M | NO | 15 | .48 |
| UC | 29 | Proctitis | 10 | M | NO | 8 | .43 |
| UC | 50 | Left sided colitis | 1 | M | NO | 7 | .85 |
| UC | 53 | Left sided colitis | 10 | M | NO | 6 | .47 |
| UC | 46 | Pancolitis | 1 | F | NO | 9 | .46 |

Figure 1

| Disease | Age | Location | Duration | Sex | ANTI-TNF | Disease activity | LRBA Quant |
|---|---|---|---|---|---|---|---|
| CD | 47 | TI | 20 | M | NO | 2 | .45 |
| CD | 59 | IC | 30 | F | NO | 4 | 1.15 |
| CD | 53 | IC | 33 | F | YES | 1 | .94 |
| CD | 43 | IC | 19 | F | YES | 5 | .95 |
| CD | 32 | IC | 3 | M | YES | 0 | .47 |
| CD | 61 | IC | 24 | F | NO | 1 | .67 |
| CD | 31 | IC | 2 | M | YES | 2 | .56 |
| CD | 44 | TI | 4 | M | NO | 15 | .21 |
| CD | 59 | TI | 10 | M | NO | 0 | .42 |
| CD | 76 | D/C | 42 | M | NO | 0 | 1.02 |
| CD | 73 | IC | 10 | M | NO | 6 | .5 |
| CD | 30 | C | 5 | F | NO | 4 | .68 |
| CD | 37 | IC | 9 | F | NO | 7 | .37 |
| CD | 48 | C | 20 | M | NO | 4 | .54 |
| CD | 25 | IC | 7 | M | YES | 6 | 1.15 |
| CD | 41 | IC | 12 | F | NO | 4 | .24 |
| CD | 63 | I | 2 | F | YES | 3 | .77 |

Figure 2

| AGE | SEX | LRBA |
|---|---|---|
| 35 | F | 1.25 |
| 49 | F | 1.46 |
| 49 | F | 1.50 |
| 45 | M | .71 |
| 38 | F | .89 |
| 32 | F | .44 |
| 26 | F | 1.02 |
| 27 | M | .72 |
| 44 | M | .70 |
| 38 | F | .92 |
| 30 | F | .58 |
| 54 | F | 1.85 |

Figure 4 a

```
            E2F                                             E2F
CCTCCGCGCCAAGAGACCCTACGGTAACTTAACAACAGCAGGAGCGCCAAAATCCCCGCC  -1368
TCAGGACTTGGCAGAAGCACCTCCCGAGGTCCGAGAGTGGGAGAGGGGAAAGTGTAGGCC  -1308
CTCGGACGGAAGGGTCTCTCCTCGCCGGGCCGGGTACACACCTGTGCTACCAGAGCAGC   -1248
GCGCCTAGTGCAGCCGGAAGCCCCAGCCCAGCACTCCGGCTGGCTCGGGCCCCCTTGGC   -1188
                                                    E2F
TGTCCGCGCGTCGTCACCGCGCCCCCGCCGCGCGGCTGCCTCCGCCTTCGCGCCCTCCCG  -1128
GCCCGCGCACTCGCGCTCGCGCACGCGCACGCCGCGCCCGGCAGCACTCGGCGCTGTCAT  -1068
                                                     Sp1
CGCGGCCGGGAGCAGCTTCAGTGGGCACACGACAGCCGCGCGACCCGTGGCGGGGCGAGC  -1008
TGTGGCAGTAGCATCCTCACCACTCGCAGCAGCCTCAGCCGCGGCGCCCGTAGCGCCAGC  -948
           NFY                    Sp1      Sp1
AGCGGCTGCTTTTGCAAAGGCTGAGCGCAGGGGCGGGGCGGGCCAGGAAGCCATGGAGTT  -888
               p300                                 Exon | Intron
CTGTGCAGCCGCGGACTCCCGGGGAGCGGACTAGGGAAACTTGGAGGCTGCGACCAGGTG  -828
           ER                                                |
CACTGACCTCTCTGTCCTCCCTTCTCTCCCTGCGGTGGCCGCTGGGTTTCTCTGGCCGCT  -768
CCCCTCCCTTCCTGCCACCACACACACCTCCCCACCCCTTCCCGTCGAATCTCAGGTGCC  -708
TGAGAGAGGTGCTTCACTCCTCCCACTGGGCCGAGCATTTAGAATAATCACCGCCCCTT   -648
                                                       Sp1
CCCCCGCCTTTTCCTGCCCTGGATCTCCGCCGCCACCTCGGTCTCGCTGCTCCTGGGCGG  -588
       ⤵                         Exon1 | Intron2
GGGGTGAGGACGAGTCCGGAGTATCTGGGTGAGGAAGAACTTTCTACCTCTGTGATAGCT  -528
TGTGGGCCCCCCTTCTTTCCTCCGATCCCTCCTTTCCCCGCGACAGTTTCTCTTTCTAGT  -468
GCACCTGTGAGGAGAGGTTACCCTGCGCCTAGAACCTGCACGAGAGTGGGGGAGGAGTGA  -408
P53                    p53                     p53
GCCTGTTCGGGGGCCTCTTGGACCTGCCTTCACCCAGAACCCAGCTTTTTGAGCCCGGGA  -348
GAAGCGGGTGGCTAGTAGTGGGGTGCCTTTAGTAACTTACTTGACCGACAATAACTATTT  -288
                                               Oct-1
CCCTCTTGTCCCCTCAAAACCCTAAAACAAAACCTAGCCTATTTAACATATATTTAATCT  -228
Intron2 | Exon2    E2F              ⤵                 NFY
TCCAATAGGGTTTGGCGTTGTTGTCAGCCTCGGGGAGAGAGATTGGACAAATATTCTCCA  -168
              NF-κB
AGAGGAGGAGGGCGACGCCAAGGACTTTCCACATCAACTGCTTTGGGGTATCTCCACAAG  -108
       ⤵                                      Oct-1
TTGGAAGAGGGACCCTTTCGTTTTGCATTGCGTGTGTTGTGCTCATTACCAGTGCAGCGA  -48
CTGCCGTCCCAGGGTGACTCTGAGTTGTCCTTTATCGTGAGCTAGCAATGGCTAGCGAA   +9
```

Figure 6

METHODS OF DETECTING AND TREATING COLON DISORDERS

CROSS-REFERENCE TO RELATED APPLICATION

This application claims the benefit of U.S. Provisional Application Ser. No. 61/104,496, filed Oct. 10, 2008, and is a continuation-in-part application of U.S. application Ser. No. 10,473,741, filed Mar. 18, 2004, which is the national stage of PCT Application No. PCT/US02/10350, filed Apr. 2, 2002, which claims the benefit of U.S. Provisional Application Ser. No. 60/280,107, filed Apr. 2, 2001, the disclosure of each of which is incorporated herein by reference in its entirety, including all figures, tables, amino acid and nucleic acid sequences.

FIELD OF THE INVENTION

This invention relates to colon disorders, such as inflammatory bowel disease. Specifically, the invention is related to a method of detecting LRBA, an indicator of colon disorders.

BACKGROUND OF THE INVENTION

The etiology of inflammatory bowel disease is not well understood; however, there is evidence to support a genetic predisposition, a triggering antigen, and an abnormal immune response. NOD 2, a Crohn's disease susceptibility gene is the best studied genetic defect thus far. NOD 2 recognizes bacterial muramyl-dipeptide which leads to increased production of NFkB and other pro-inflammatory mediators. TLR4 is part of the innate immune system and seems to regulate the response towards enteric bacteria, specifically lipopolysaccharide (LPS), which is a component of gram negative bacterial cell walls (Gribar, S. C., et al. The role of epithelial Toll-like receptor signaling in the pathogenesis of intestinal inflammation. *J. Leukoc Biol.* 2008 March; 83(3):493-8). Enteric bacteria are thought to be the antigenic stimuli in inflammatory bowel disease (IBD). Specific genetic defects are likely responsible for the different phenotypic characteristics of IBD.

Lipopolysaccharide is a potent inducer of B cells, monocytes, and dendritic cells. Stimulation of these cells leads to the production of inflammatory cytokines so that the cells can participate in the immune response to bacterial pathogens (Wang, J. W., et al. Identification of a novel lipopolysaccharide-inducible gene with key features of both A kinase anchor proteins and chs1/beige proteins. *J Immunol.* 2001 Apr. 1; 166(7):4586; Kerr, W. G., et al. Transcriptionally defective retroviruses containing lacZ for the in situ detection of endogenous genes and developmentally regulated chromatin. Cold Spring Harbor Symposia on Quantitative Biology. 1989: 54, 767-776). In order to identify genes involved in the maturation of immune cells, a gene-trapping system using LPS as a stimulant of lymphocyte differentiation was developed. Several novel LPS responsive genes were successfully trapped from mammalian cells, including Lipopolysaccharide Responsive Beige-like Anchor (LRBA). (Kerr, W. G., et al. Analysis of lipopolysaccharide-response genes in B-lineage cells demonstrates that they can have differentiation stage-restricted expression and contain SH2 domains. Proc Natl Acad Sci. Vol 93 p. 3947-52; Kerr, W. G., et al. Cold Spring Harbor Symposia on Quantitative Biology. 1989: 54, 767-776). LRBA is involved in guiding intracellular vesicles to activated receptor complexes, facilitating polarized secretion and/or membrane deposition of immune effector molecules. The gene was then cloned and its promoter was studied; revealing binding sites for NFkB, p53 and E2F (Wang, J. W., et al. Deregulated expression of LRBA facilitates cancer cell growth. Oncogene. 2004 May 20; 23(23):4089-97).

The novel LPS-gene trapping system serves as an excellent tool to help identify genes that are involved in the immune regulation of bacteria (Kerr, W. G., et al. Proc Natl Acad Sci. Vol 93 p. 3947-52; Kerr, W. G., et al. Cold Spring Harbor Symposia on Quantitative Biology. 1989: 54, 767-776). Based on homology to the CHS1/BG gene and Protein Kinase A anchor proteins, LRBA and its paralogues (collectively referred to as the WBW gene family) are involved in directing trafficking of intracellular vesicles to activated receptor complexes and thus facilitating polarized secretion and/or membrane deposition of effector molecules in both the immune system and nervous system. There are at least three different isoforms of LRBA and the ratio of these isoforms varies dramatically in different tissues (Wang, J. W., et al. J Immunol. 2001 Apr. 1; 166(7):4586).

BRIEF SUMMARY OF THE INVENTION

Disclosed is a method of identifying a colon disorder such as inflammatory bowel disease (IBD) in a subject. Enteric bacteria are thought to be the antigenic stimuli in IBD. Lipopolysaccharide (LPS) is recognized by Toll-like receptor 4, which induces the innate immune system in response to enteric bacteria. A gene-trapping system using LPS as the trigger was developed and revealed the Lipopolysaccharide-Responsive Beige-like Anchor (LRBA) gene. Binding sites for nuclear factor (NF)-κB, p53, and E2F were noted within the promoter region of LRBA. LRBA is involved in guiding intracellular vesicles to activated receptor complexes, and thus facilitates polarized secretion and/or membrane deposition of immune effector molecules. The inventors hypothesized that LRBA is involved in the recognition of enteric bacteria and that breakdown in this pathway contributes to IBD.

Real-time polymerase chain reaction (PCR) was performed on mRNA isolated from leukocytes of human subjects with IBD. LRBA expression was compared with that in leukocytes from unaffected controls. The Harvey-Bradshaw Index and the modified Truelove and Witts Severity Index were calculated to evaluate the effects of disease activity on LRBA expression. Multivariate analysis was used to identify statistically significant differences. 17 patients with Crohn's disease, and 5 patients with ulcerative colitis were studied, with 12 controls. The quantitative expression of LRBA ranged from 0.45 to 1.85 in the controls, 0.21 to 1.15 in patients with Crohn's disease, and 0.43 to 0.85 in patients with ulcerative colitis. Mean LRBA expression was 34% lower in the Crohn's disease group and 45% lower in the ulcerative colitis group compared with the controls. The analysis of variance test revealed an F-value of 4.77 with a p-value of 0.0156, indicating statistical significance. The Tukey test identified statistical significance at the 95% confidence levels for both the Crohn's disease and the ulcerative colitis groups compared with controls. The underexpression of LRBA in patients with IBD may help explain the dysregulated immune response toward enteric bacteria observed in these patients.

The LRBA gene was isolated by LPS-gene trapping. LRBA gene expression was analyzed for each individual by real time quantitative RT-PCR and compared to disease activity, showing mean LRBA expression 34% lower in the Crohn's group and 45% lower in the ulcerative colitis group compared with controls. This indicates LRBA is underexpressed in Crohn's and ulcerative colitis groups when compared to controls, explaining the dysregulated immune response towards enteric bacteria observed in inflammatory bowel disease.

One aspect of the invention provides a method of detecting a colon disorder in a subject, comprising obtaining a sample comprising peripheral blood mononuclear cells (PBMCs) from the subject, and determining whether LRBA is underexpressed in the PBMCs (e.g., relative to a an appropriate control), wherein LRBA underexpression is indicative of the colon disorder. Optionally, the determined LRBA can be compared to a control known to have one or more colon disorders. Colon disorders that may be detected include, for example, inflammatory bowel disease (such as Crohn's disease or ulcerative colitis) and colon cancer. The sample may be any biological sample comprising PBMCs (e.g., leukocytes), such as whole blood. Advantageously, the invention may be used to test for a colon disorder using a blood sample from a subject before a more invasive test for colon disorders is employed. Optionally, the method further comprises carrying at least one confirmatory test for the colon disorder if LRBA is determined to be underexpressed. Examples of confirmatory tests for colon disorders include, but are not limited to, a blood test, test for blood in a stool sample, test for a target microorganism in a stool sample, colonoscopy, sigmoidoscopy, X-ray with barium, computerized axial tomography, and capsule tomography, or a combination of two or more of the foregoing.

Another aspect of the invention concerns a method of treating a colon disorder in a subject determined to have underexpressed LRBA. The method comprises obtaining a sample comprising PBMCs from the subject; determining whether LRBA is underexpressed in the PBMCs (e.g., relative to an appropriate control), wherein LRBA underexpression is indicative of the colon disorder; and treating the subject with a therapy for the colon disorder if LRBA is underexpressed. Optionally, the determined LRBA can be compared to a control known to have one or more colon disorders. Optionally, the method further comprises carrying out at least one confirmatory test for the colon disorder if LRBA is determined to be underexpressed. Examples of confirmatory tests for colon disorders include, but are not limited to, a blood test, test for blood in a stool sample, test for a target microorganism in a stool sample, colonoscopy, sigmoidoscopy, X-ray with barium, computerized axial tomography, and capsule tomography, or a combination of two or more of the foregoing.

The therapy or therapies used for treating the subject determined to be suffering from a colon disorder can be selected by a physician and will depend upon the colon disorder in question (e.g., ulcerative colitis, Crohn's disease, colon cancer). For example the therapy may comprise bowel diversion surgery, administration of an anti-inflammatory, administration of an antibiotic, administration of an anti-diarrheal, administration of a laxative, administration of a pain reliever, or a combination of two or more of the foregoing. In cases in which the colon disorder is cancer, the therapy can be, for example, bowel diversion therapy, a chemotherapeutic, and radiation therapy, or a combination of two or more of the foregoing. These and other appropriate treatment regimens and procedures that may used for treatment of colon disorders are known to those of ordinary skill in the art.

Another aspect of the invention concerns a method of determining the expression of LRBA in PBMCs, comprising obtaining a sample comprising PBMCs from a subject, and determining the amount of LRBA messenger RNA or protein in the PBMCs.

Another aspect of the invention concerns, a method of treating a colon disorder in a subject, comprising obtaining a sample comprising peripheral blood mononuclear cells (PBMCs) from the subject, determining whether LRBA is underexpressed in the PBMCs (e.g., relative to an appropriate control), wherein LRBA underexpression is indicative of the colon disorder, and advising the subject of treatment options for treating the colon disorder if LRBA is underexpressed (e.g., verbally, in writing, or other forms of communication). Optionally, the method further comprises carrying out at least one confirmatory test for the colon disorder if LRBA is determined to be underexpressed. Optionally, the method further comprises treating the colon disorder if LRBA is underexpressed and, optionally, if a confirmatory test is carried out that indicates the presence of a colon disorder.

Another aspect of the invention concerns an in vitro polymerase chain reaction (PCR) assay kit for determining whether a subject has a colon disorder by detecting underexpression of Lipopolysaccharide Responsive Beige-like Anchor (LRBA), said kit comprising a first container comprising PCR primers that amplify an LRBA transcript or cDNA generated therefrom; and a second container comprising a nucleic acid marker, said marker being and labeled and able to hybridize to said transcript or cDNA.

BRIEF DESCRIPTION OF THE DRAWINGS

For a fuller understanding of the invention, reference should be made to the following detailed description, taken in connection with the accompanying drawings, in which:

FIG. 1 shows the normalized ulcerative colitis characteristics and normalized LRBA quantification.

FIG. 2 shows individual Crohn's disease characteristics and normalized. LRBA quantification.

FIG. 4 shows individual controls normalized LRBA quantification.

FIG. 6 shows a sequence of the LRBA promoter, showing NF-κB, p53, and E2f binding sites (SEQ ID NO:1).

BRIEF DESCRIPTION OF THE SEQUENCES

Figure 3:
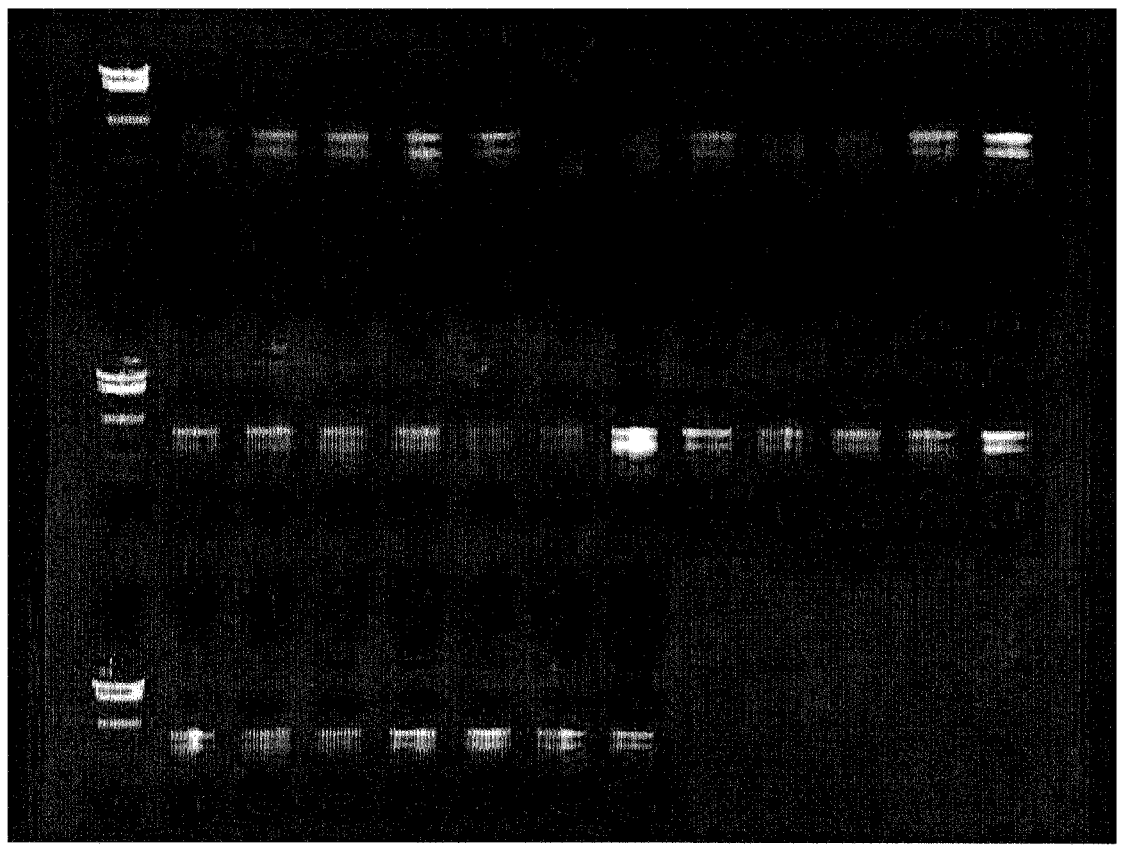
FIG. 3 shows gel electrophoresis of isolated RNA. RNA was isolated from leukocytes of patients with IBD and controls.

SEQ ID NO: 1 is a sequence of the LRBA promoter.

DETAILED DISCLOSURE OF THE INVENTION

The method is particularly applicable to the diagnosis of inflammatory bowel disease, such as ulcerative colitis and Crohn's disease. The sample on which the assay is performed is preferably of body tissue or body fluid, but may be cells cultured in vitro. The sample may be a piece of tissue or a fine needle aspirate (FNA) of cells from a subject. Preferably, the biological sample is a sample of peripheral blood or other body fluid containing PBMCs. The subject may be presenting with symptoms of a colon disorder at the time the sample is taken from the subject and/or LRBA expression determined, or the subject may be asymptomatic.

LRBA cDNA may be detected by use of one or more labeled specific oligonucleotide probes, the probes being chosen so as to be capable of annealing to part of the amplified cDNA sequence. Alternatively, labeled oligonucleotide primers and/or labeled mononucleotides could be used. There are a number of suitable detectable labels, which can be employed, including radiolabels.

The level of gene expression of LRBA can be determined by RT-PCR, or by using labeled antibodies that bind to LRBA protein, or other methods known in the art for determination of messenger RNA or protein. For example, labeled antibodies that bind to LRBA can be used to stain cells expressing the proteins. If the cells normally express the LRBA protein but the antibodies to LRBA do not hind to the cells as indicated by the lack of production of the desired stain or other label (or diminished stain or other label), this indicates that LRBA is not expressed (or underexpressed) by the cells and that the subject has a colon disorder, such as ulcerative colitis or Crohn's disease.

U.S. Patent Publication 2004/0235765 (Kerr et al., entitled "LPS-Responsive CHS1/Beige-Like Anchor Gene and Therapeutic Applications Thereof", published Nov. 25, 2004); Wang J-W et al. ("Deregulated Expression of LRBA Facilitates Cancer Cell Growth", Oncogene, 2004, 23; 4089-4097, published online Apr. 5, 2004); and Wang J-W et al. ("Identification of a Novel Lipopolysaccharide-Inducible Gene with Key Features of Both A Kinase Anchor Proteins and Chs1/Beige Proteins", *J. Immunol.* 2001, 166(7):4586-4595); GenBank Accession Number AAG48558.2 (Nov. 5, 2001; Version AAG48558.2; GI: 16716613); GenBank Accession Number EAX04996 (Dec. 18, 2006; Version EAX04996.1; GI: 119625401); GenBank Accession Number BC064834 (Jan. 3, 2005; Version BC064834.1; GI: 40675311); GenBank Accession Number AF467287 (Aug. 7, 2002; Version AF467287.1; GI: 21434740); and GenBank Accession Number AF216648 (Nov. 5, 2001; Version AF216648.2; GI: 16716612) are each incorporated herein by reference in their entirety.

In some embodiments, the subject is predisposed to a colon disorder, such as ulcerative colitis or Crohn's disease. In some embodiments, the subject is presenting one or more symptoms associated with a colon disorder (symptomatic). In some embodiments, the subject is not presenting symptoms associated with a colon disorder (asymptomatic).

In some embodiments, the subject is not suffering from cancer. In some embodiments, the colon disorder is not colon cancer, or other cancer, tumor, and/or malignancy of the colon or gastrointestinal tract.

Detecting a Colon Disorder

According to the present invention, a colon disorder can be detected by determining whether or not LRBA is expressed in a tissue type, such as blood, that normally expresses LRBA, and to what extent. There are a number of ways to determine this including the use of antibodies to detect the presence of the proteins or by determining the presence and amount mRNA coding for LRBA. Gene expression analysis can be performed at the mRNA or protein level to detect differences in LRBA gene expression between populations of target cells (e.g., PBMCs) of a subject and reference cells (e.g., an appropriate control) to determine whether or not LRBA is being expressed and to what extent. LRBA expression can be determined in multiple samples taken at different time points to monitor LRBA expression.

The methods of detecting colon disorders of the invention are preferably performed using human biological samples. The target cell population may include one or more subpopulations of PBMCs (e.g., lymphocytes, monocytes, etc.). Preferably, the biological sample is a blood sample containing peripheral blood mononuclear cells (PBMC), such as whole blood. Appropriate isolation steps may be taken, and/or pre-treatments carried out, to determine LRBA expression in the target cell type or types. The samples may be preserved or pre-treated, or prepared for histological and immunohistochemical analysis. Red blood cells can by lysed by treatment with hypotonic solutions from nucleated cells, and separation can be achieved by differential centrifugation and other methods known in the art. For example, a Ficoll-step-gradient procedure can be utilized. PBMC-enriched cell populations can be obtained using the buffy coat method. Biological samples may be cryopreserved prior to determination of LRBA expression.

Use of Immunological Reagents to Detect the Expression of LRBA

For the purposes of this invention, the term "immunological reagents" is intended to encompass antisera and antibodies, particularly monoclonal antibodies, as well as fragments thereof (including F(ab), F(ab)$_2$, F(ab)' and F$_v$ fragments) that bind to LRBA. Also included in the definition of immunological reagent are chimeric antibodies, humanized antibodies, and recombinantly-produced antibodies and fragments thereof, as well as aptamers (i.e., oligonucleotides capable of interacting with target molecules such as peptides). Immunological methods used in conjunction with the reagents of the invention include direct and indirect (for example, sandwich-type) labeling techniques, immunoaffinity columns, immunomagnetic beads, fluorescence activated cell sorting (FACS), enzyme-linked immunosorbent assays (ELISA), and radioimmune assay (RIA), most preferably FACS. For use in these assays, the immunological reagents can be labeled, using fluorescence, antigenic, radioisotopic or biotin labels, among others, or a labeled secondary or tertiary immunological detection reagent can be used to detect binding of the immunological reagents (e.g., in secondary antibody (sandwich) assays) used in determining the presence of LRBA. Examples of immunological reagents useful in the practice of this invention include antibodies, most preferably monoclonal antibodies that recognize LRBA. The immunological reagent may be specific to one or more isoforms of LRBA. Preferably, the immunological reagent is not specific with respect to LRBA isoform (i.e., binding to all LRBA isoforms, or at least the major LRBA isoforms).

The immunological reagents employed in the invention are preferably detectably-labeled, most preferably using fluorescent labels that have excitation and emission wavelengths adapted for detection using commercially-available instruments such as and most preferably fluorescence activated cell sorters. Examples of fluorescent labels useful in the practice of the invention include phycoerythrin (PE), fluorescein isothiocyanate (FITC), rhodamine (RH), Texas Red (TX), Cy3, Hoechst 33258, and 4',6-diamidino-2-phenylindole (DAPI). Such labels can be conjugated to immunological reagents, such as antibodies and most preferably monoclonal antibodies using standard techniques.

In addition to the use of immunological methods for detection and determination of LRBA protein (e.g., ELISA, Western blots, immunoprecipitation), other detection methods for proteins that can be utilized to determine LRBA expression include, but are not limited to, mass spectrometry, protein array, and 2-D gel electrophoresis. For example, surface-enhanced laser desorption/ionization time-of-flight mass spectrometry (SELDI-TOF MS) allows rapid generation of high-throughput protein profiles from a large number of samples (see, for example, Liu et al., *Cancer Invest.* 2006, 24:747-753; Munro et al., *Int. J. Cancer.* 2006, 119:2642-2650; Simpkins et al., *Pharmacogenomics.* 2005, 6(6):647-653; Oh et al., *Genome Inform.* 2005, 16:195-204; Lakhan S. E., *Diagn Pathol.* 2006, 1:11; Novikova et al., *Neurobiol Dis.* 2006, 23:61-76; Lewczuk et al., *Biol Psychiatiy.* 2004, 55:524-530; and Sanchez et al., *Proteomics*. 2004, 4:2229-2233, which are each incorporated herein by reference in its entirety).

Detection of LRBA Using Nucleic Acid Hybridization Techniques

The expression of LRBA can be determined using nucleic acids and associated hybridization methods to detect the presence of mRNA within a cell of interest. For example, a nucleic acid that is complementary to and hybridizes under stringent conditions to the mRNA of a portion of LRBA can be detectably labeled. Such a detectably labeled nucleic acid molecule can be contacted with a cell or an extract of a cell to detect the presence and amount of the mRNA that encodes LRBA. The amount of nucleic acids that encode LRBA is assumed to correlate with the expression of the LRBA in a cell. The selection of an appropriate nucleic acid molecules for use as a probe can be made by studying the nucleic acid sequences of human LRBA and determining an appropriate length. A unique sequence should be determined that selectively hybridizes under stringent conditions to the mRNA of LRBA. The probe may be specific to one or more isoforms of LRBA. Preferably, the probe is not specific with respect to LRBA isoform (i.e., detecting all LRBA isoforms, or at least the major LRBA isoforms).

The term "stringent conditions" as used herein refers to parameters with which the art is familiar. Nucleic acid hybridization parameters may be found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, stringent conditions, as used herein, refers, for example, to hybridization at 65 degrees C. in hybridization buffer (3.5×SSC, 0.02% Ficoll, 0.02% polyvinyl pyrrolidone, 0.02% Bovine Serum Albumin, 2.5 mM $NaH_2PO_4$ (pH 7), 0.5% SDS, 2 mM EDTA). SSC is 0.15 M sodium chloride/ 0.015 M sodium citrate, pH 7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68 degrees C.

There are other conditions, reagents, and so forth which can be used, which result in a similar degree of stringency. The skilled artisan will be familiar with such conditions, and thus they are not provided here. It will be understood, however, that the skilled artisan will be able to manipulate the conditions in a manner to permit the clear identification of LRBA (e.g., by using lower stringency conditions). The skilled artisan also is familiar with the methodology for screening cells and libraries for expression of such molecules which then are routinely isolated, followed by isolation of the pertinent nucleic acid molecule and sequencing.

One method for detecting the LRBA transcripts in genetic material derived from PBMCs uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990). Applications of PCR technology are disclosed in "Polymerase Chain Reaction" Erlich, H. A., et al., Eds. Cold Spring Harbor Press, Cold Spring Harbor, N.Y. (1989). U.S. Pat. No. 4,683,202, U.S. Pat. No. 4,683,195, U.S. Pat. No. 4,965,188 and U.S. Pat. No. 5,075,216 describe methods of performing PCR. PCR may be routinely practiced using Perkin Elmer Cetus GENE AMP RNA PCR kit.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

PCR primers can be designed routinely by those having ordinary skill in the art using sequence information. The nucleotide sequences of LRBA transcripts are known in the art. To perform this method, RNA is extracted from cells in a sample and tested or used to make cDNA using well known methods and readily available starting materials.

Those having ordinary skill in the art can readily prepare PCR primers. A set of primers generally contains two primers. When performing PCR on extracted mRNA or cDNA generated therefrom, if the LRBA transcript or cDNA generated therefrom is present, multiple copies of the mRNA or cDNA will be made. If it is not present, PCR will not generate a discrete detectable product. Primers are generally 8-50 nucleotides, preferably about 15-35 nucleotides, more preferably 18-28 nucleotides, which are identical or complementary to and therefor hybridize to the LRBA transcript or cDNA generated therefrom. In preferred embodiments, the primers are each 15-35 nucleotides in length, and more preferably 18-28 nucleotides in length. The primer must hybridize to the sequence to be amplified.

Typical primers are 18-28 nucleotides in length and generally have 500 to 60% G+C composition. The entire primer is preferably complementary to the sequence to which it must hybridize. Preferably, primers generate PCR products 100 base pairs to 2000 base pairs. However, it is possible to generate products of 50 to up to 10 kb and more. If mRNA is used as a template, the primers must hybridize to mRNA sequences. If cDNA is used as a template, the primers must hybridize to cDNA sequences.

The mRNA or cDNA is combined with the primers, free nucleotides and enzyme following standard PCR protocols. The mixture undergoes a series of temperature changes. If the LRBA transcript or cDNA generated therefrom is present, that is, if both primers hybridize to sequences on the same molecule, the molecule comprising the primers and the intervening complementary sequences will be exponentially amplified. The amplified DNA can be easily detected by a variety of well known means. If no LRBA transcript or cDNA generated therefrom is present, no PCR product will be exponentially amplified. The PCR technology therefore provides an extremely easy, straightforward and reliable method of detecting the LRBA transcript in a sample.

PCR product may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes diagnostic kits comprising oligonucleotides which are useful as primers for performing PCR methods to amplify the LRBA transcript or cDNA generated therefrom.

According to the invention, diagnostic kits can be assembled which are useful to practice methods of detecting the presence of the LRBA transcript or cDNA generated therefrom in biological samples containing PBMCs, such as whole blood. Such diagnostic kits comprise oligonucleotides which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the LRBA transcript or cDNA generated therefrom. Additional components in some kits include instructions for carrying out the assay. Additionally, the kit may optionally comprise depictions or photographs that represent the appearance of positive and negative results.

PCR assays are useful for detecting the LRBA transcript in homogenized tissue samples and cells in body fluid samples, such as blood.

Another method of determining whether a sample contains cells expressing LRBA is by branched chain oligonucleotide hybridization analysis of mRNA extracted from a sample. Branched chain oligonucleotide hybridization may be performed as described in U.S. Pat. No. 5,597,909, U.S. Pat. No. 5,437,977 and U.S. Pat. No. 5,430,138, which are each incorporated herein by reference. Reagents may be designed following the teachings of those patents and that sequence of the LRBA transcript.

Another method of determining whether a sample contains cells expressing LRBA is by Northern Blot analysis of mRNA extracted from a biological sample, such as blood. The techniques for performing Northern blot analyses are well known by those having ordinary skill in the art and are described in Sambrook, J. et al., (1989) Molecular Cloning: A Laboratory Manual, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

The mRNA is extracted using poly dT columns and the material is separated by electrophoresis and, for example, transferred to nitrocellulose paper. Labeled probes made from an isolated specific fragment or fragments can be used to visualize the presence of a complementary fragment fixed to the paper. Probes useful to identify mRNA in a Northern Blot have a nucleotide sequence that is complementary to the LRBA transcript. Those having ordinary skill in the art can use the sequence information included herein to design such probes or to isolate and clone the LRBA transcript or cDNA generated therefrom to be used as a probe. Such probes are at generally least 15 nucleotides, preferably 30-200, more preferably 40-100 nucleotide fragments and may be the entire LRBA transcript.

According to the invention, diagnostic kits can be assembled which are useful to practice methods of detecting the presence of the LRBA transcript in biological samples by Northern blot analysis. Such diagnostic kits comprise oligonucleotides which are useful as probes for hybridizing to the mRNA. The probes may be radiolabeled. It is preferred that diagnostic kits according to the present invention comprise a container comprising a size marker to be run as a standard on a gel. It is preferred that diagnostic kits according to the present invention comprise a container comprising a positive control which will hybridize to the probe. Additional components in some kits include instructions for carrying out the assay (e.g., written or embossed on packaging or on one or more containers). Additionally, the kit may optionally comprise depictions or photographs that represent the appearance of positive and negative results. Northern blot analysis is useful for detecting the LRBA transcript in homogenized tissue samples and cells in body fluid samples.

Another method of detecting the presence of the LRBA transcript by oligonucleotide hybridization technology. Oligonucleotide hybridization technology is well known to those having ordinary skill in the art. Briefly, detectable probes which contain a specific nucleotide sequence that will hybridize to nucleotide sequence of the LRBA transcript. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences.

Probes useful in oligonucleotide assays at least 18 nucleotides of complementary DNA and may be as large as a complete complementary sequence to the LRBA transcript. In some preferred embodiments the probes of the invention are 30-200 nucleotides, preferably 40-100 nucleotides.

One having ordinary skill in the art, using the human LRBA sequence information disclosed herein can design probes which are fully complementary to the LRBA transcript. Hybridization conditions can be routinely optimized to minimize background signal by non-fully complementary hybridization. In some preferred embodiments, the probes are full length clones. Probes are at least 15 nucleotides, preferably 30-200, more preferably 40-100 nucleotide fragments and may be the entire LRBA transcript.

The present invention includes labeled oligonucleotides which are useful as probes for performing oligonucleotide hybridization. That is, they are fully complementary with the LRBA transcript. For example, the mRNA sequence includes portions encoded by different exons. The labeled probes of the present invention are labeled with radiolabeled nucleotides or are otherwise detectable by readily available nonradioactive detection systems.

According to the invention, diagnostic kits can be assembled which are useful to practice oligonucleotide hybridization methods of the invention. Such diagnostic kits comprise a labeled oligonucleotide which encodes portions of the LRBA transcript. It is preferred that labeled probes of the oligonucleotide diagnostic kits according to the present invention are labeled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample. Additional components in some kits include instructions for carrying out the assay. Additionally the kit may optionally comprise depictions or photographs that represent the appearance of positive and negative results. Oligonucleotide hybridization techniques are useful for detecting the LRBA transcript in homogenized tissue samples and cells in body fluid samples.

Thus, the present invention relates to in vitro kits for evaluating biological samples to determine the level of LRBA (e.g., LRBA mRNA, LRBA protein, LRBA activity) and to reagents and compositions useful to practice the same. Techniques for determining the presence of mRNA of a polypeptide have resulted in the production of various microarrays, bioarray, biochips and biochip arrays, which may be employed with the invention. As used herein, the terms "microarray," "bioarray," "biochip" and "biochip array" refer to an ordered spatial arrangement of immobilized biomolecular probes arrayed on a solid supporting substrate. Preferably, the biomolecular probes are immobilized on second linker moieties in contact with polymeric beads, wherein the polymeric beads are immobilized on first linker moieties in contact with the solid supporting substrate. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence of a nucleic acid that encodes LRBA. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors). Useful microarrays for detecting differential gene expression are described, for example, in U.S. Pat. No. 6,040,138 to Lockhart et al. (commercially-available from Affymetrix, Inc., Santa Clara, Calif.) and U.S. Pat. No. 6,004,755 to Wang (commercially-available from Incyte Inc., Palo Alto, Calif.) and are also commercially available, inter alia, from Research Genetics (Huntsville, Ala.).

Gene expression analysis can be performed to detect differences in gene expression between populations of target cells (e.g., PBMCs) of a subject and reference cells (e.g., an appropriate control) to determine whether or not LRBA is being expressed and to what extent. The target cell population may include one or more subpopulations of PBMCs (e.g., lymphocytes, monocytes, etc.). Hybridization of gene expression microarrays can be used to produce patterns of gene expression of LRBA. Identification of genes and patterns of genes differentially expressed in the target cells is established by comparison of the gene expression pattern obtained by performing the microarray hybridization analysis on cDNA from target cells in comparison to that of normal cells.

In some embodiments, various methodologies of the instant invention include a step that involves comparing LRBA in a sample obtained from a subject to a "suitable control," also referred to interchangeably herein as an "appropriate control." Thus, in accordance with the invention, it can be determined whether a subject has, or more likely to have, a colon disorder such as Crohn's disease or ulcerative colitis, based on LRBA expression in PBMCs from the subject (e.g., based on comparison to an appropriate control). "suitable control" or "appropriate control" in this context is a predetermined value associated with LRBA useful for comparison purposes, which can take many different forms. Exemplary forms include, but are not limited to, for example, a transcription rate, mRNA level, translation rate, protein level, protein structure, biological activity, cellular characteristic or property, genotype, phenotype, enzymatic activity etc. associated with LRBA. In one embodiment, a "suitable control" is a predetermined LRBA activity, which is compared to LRBA activity in a sample obtained from a subject being identified as having or not having a colon disorder as described herein. In another embodiment, a "suitable control" is a predetermined LRBA level, which is compared to an LRBA level in a sample obtained from a subject being identified as having or not having a colon disorder as described herein. In another embodiment, a "suitable control" is a predetermined LRBA level, which is compared to an LRBA level in a sample derived from a subject in which a clinical measure was achieved, for example an LRBA level obtained from cells in a subject who reached or failed to reach a particular clinical outcome following treatment of the colon disorder.

In some embodiments, a "suitable control" or an "appropriate control" can be a single cut-off value, such as a median or mean. A single cut-off value can be established, for example, based upon comparative groups, such as in groups having an LRBA level or activity which correlates with lack of, or resistance to, a colon disorder, and groups having an LRBA level or activity which does not confer or correlate with resistance to lack of, or resistance to, a colon disorder. For example, samples containing PBMCs such as leukocytes can be obtained from various individuals or blood banks and an LRBA level or activity can be measured in each sample. Consequently, a single cut-off value can be based on the mean of an LRBA level or activity in samples which correlate with lack of, or resistance to, a colon disorder. Another comparative group can be, for example, an LRBA level or activity in a group of individuals with a family history of colon disorder, or a family history with a lack of, resistance to, a colon disorder. Optionally, the determined LRBA can be compared to a control in which the control is an LRBA level or activity from a subject, or a mean LRBA level or activity from a group of subjects, known to have one or more colon disorders. In practice, the readout or output for determination of LRBA may be qualitative, quantitative, or semi-quantitative. Preferably, a quantitative value of LRBA level or activity is determined, which is compared to that of an appropriate control.

The terms "treat," "treating," and "treatment," as used herein, refer to therapeutic or preventative measures described herein. The methods of "treatment" employ administration to a subject identified using methods of the present invention, for example, a subject having a inflammatory bowel disease or other colon disorder, a treatment or procedure, in order to prevent, cure, delay, reduce the severity of, or ameliorate one or more symptoms of the colon disorder, or in order to prolong the survival of a subject beyond that expected in the absence of such treatment.

The term "subject" and "patient", as used herein, refers to a human or non-human mammals, of any age or gender.

Without wishing to be bound by theory, it is contemplated that, any suitable characteristic associated with LRBA such as, for example, mRNA level, polypeptide amount, LRBA activity, transcription rate, translation rate etc., may be used as an indicator for identifying subjects that are suffering from a colon disorder. In some embodiments, LRBA level, for example, amount of LRBA polypeptide present is used as an indicator for identifying subjects suitable for a further diagnostic test, such as a colonoscopy. In other embodiments, LRBA activity is used as an indicator for identifying subjects suitable for treatment of a colon disorder.

Materials and Methods

Study Subjects

Patients were recruited at the University of South Florida Medical Clinic with informed consent approved by the Institutional Review Board. They included 17 patients with Crohn's disease, 5 with ulcerative colitis and 12 controls. Diagnosis was confirmed by chart review of endoscopic, radiologic, histologic and clinical criteria based on the World Health Organization and the International Organization for the Study of Inflammatory Bowel Disease (Shinzaki S, et al. IgG oligosaccharide alterations are a novel diagnostic marker for disease activity and the clinical course of inflammatory bowel disease. Am J Gastroenterol. 2008 May; 103(5):1173-81). Disease activity was based on the Harvey-Bradshaw Index for the Crohn's patients and the Modified Mayo-Clinic score for ulcerative colitis group (Best W R. Predicting the Crohn's disease activity index from the Harvey-Bradshaw Index. Inflamm Bowel Dis. 2006 April; 12(4):304-10; Sandborn, W. J., et al. MMX Multi Matrix System mesalazine for the induction of remission in patients with mild-to-moderate ulcerative colitis: a combined analysis of two randomized, double-blind, placebo-controlled trials. Aliment Pharmocol Ther. 2007 Jul. 15; 26(2):205-15). Patient characteristics, including controls, are presented in Table 1. Controls had no history of inflammatory bowel disease, autoimmune disorders or known family history of inflammatory bowel disease.

Peripheral Leukocyte Isolation and Total RNA Purification

PAXgene Blood RNA Tubes (Qiagen) were used to collect blood samples. The tubes were incubated for at least 2 hours at room temperature after blood draw to ensure complete lysis of blood cells. The PAXgene RNA purification protocol and kit were used to isolate the RNA. Briefly, after the RNA was isolated it was washed with ethanol and treated with DNase 1 to degrade any remaining DNA. An elution step was completed and the samples were immediately denatured for use in down stream applications. Spectroscopy and gel electrophoresis were performed to document high quality RNA.

cDNA Reactions

Reverse Transcriptase (RT) reactions were random hexamer-primed using Applied Biosystems' (Foster City, Calif.) High Capacity cDNA Archive Kit. (All RT reactions were done at the same time so that the same reactions could be used for all gene studies.) For the construction of standard curves, serial dilutions of pooled sample RNA were used (50, 10, 2, 0.4, 0.08, and 0.016 ng) per reverse transcriptase reaction. One "no RNA" control and one "no reverse transcriptase" control was included for the standard curve. Three reactions were performed for each sample: 10 ng, 0.8 ng, and a no RT (10 ng) control.

Real-Time Polymerase Chain Reactions (PCR)

Gene expression assays were performed using assay primer and probe sequences in the TaqMan® Gene Expression Assay system (Applied Biosystems). The probe is labeled with 6-carboxy-fluorescein as the reporter on the 5' end, and a non-fluorescent quencher plus a minor-groove binder on the 3'-end.

Real-time quantitative PCR analyses were performed using the ABI PRISM 7900HT Sequence Detection System (Applied Biosystems). All standards were tested in multiple wells (2 wells/plate×4 plates), except the no template control ($H_2O$), the no RT control, the no RNA control, and the no amplification control (Bluescript plasmid) which were tested in quadruplicate wells (1 well/plate×4 plates). All samples were tested in triplicate wells. The no RT controls were tested in duplicate wells.

PCR was carried out with the TaqMan Universal PCR Master Mix (Applied Biosystems) using 2 μl of cDNA and 1× primers & probe in a 20-μl final reaction mixture. After a 2-min incubation at 50° C., AmpliTaq Gold was activated by a 10-min incubation at 95° C., followed by 40 PCR cycles consisting of 15 s of denaturation at 95° C. and hybridization of probe and primers for 1 min at 60° C. Data was analyzed using SDS software version 2.2.2.

Statistical Analysis

The analysis of variance test was utilized to identify a significant difference between the means of LRBA expression in the Crohn's, ulcerative colitis and control groups. The Tukey test identified the groups that differed and whether they were statistically significant.

The invention will be further described in the following examples, which are not meant to limit the scope of the invention in any way.

Example 1

Differential Expression of LRBA

Baseline characteristics were collected on the patients, as seen in Table 1. There were 5 ulcerative colitis patients; 4 male and 1 female, seen in FIG. 1(A). Ages ranged from 29-53 with a mean of 42 years old. The Revised Mayo Clinic score ranged from 6-15 with an average of 9. Remission is defined as <10. Disease location was pancolonic 2/5, left sided 2/5 and proctitis 1/5. Controls age ranged from 26-54 with an average of 39 years old. Seventeen Crohn's patients were enrolled; 9 male and 8 female, seen in FIG. 2. Ages ranged from 25-76, with a mean of 48 years old. The Harvey-Bradshaw index ranged from 0-15 with an average of 4. Remission is defined as <5. Disease was located in the ileum/colon in 9/17, small bowel only 3/17, colon only 4/17, and duodenum/colon 1/17.

TABLE 1

Summary of baseline characteristics: IBD and control patients

| | Ulcerative Colitis | Crohn's Disease | Control |
|---|---|---|---|
| Number of patients | 5 | 17 | 12 |
| Mean (range) age | 42 (29-53) years | 48 (25-76) years | 39 (26-54) years |
| Average Disease Duration | 5 years | 16 years | — |
| Anti-TNF medications | 0 patients | 5 patients | — |
| Mean (range) disease activity score | 9 (6-15) points | 4 (0-15) points | — |
| Remission defined as a Truelove and Witt Severity Index Score | <10 points | <5 points | — |

Figure 5:
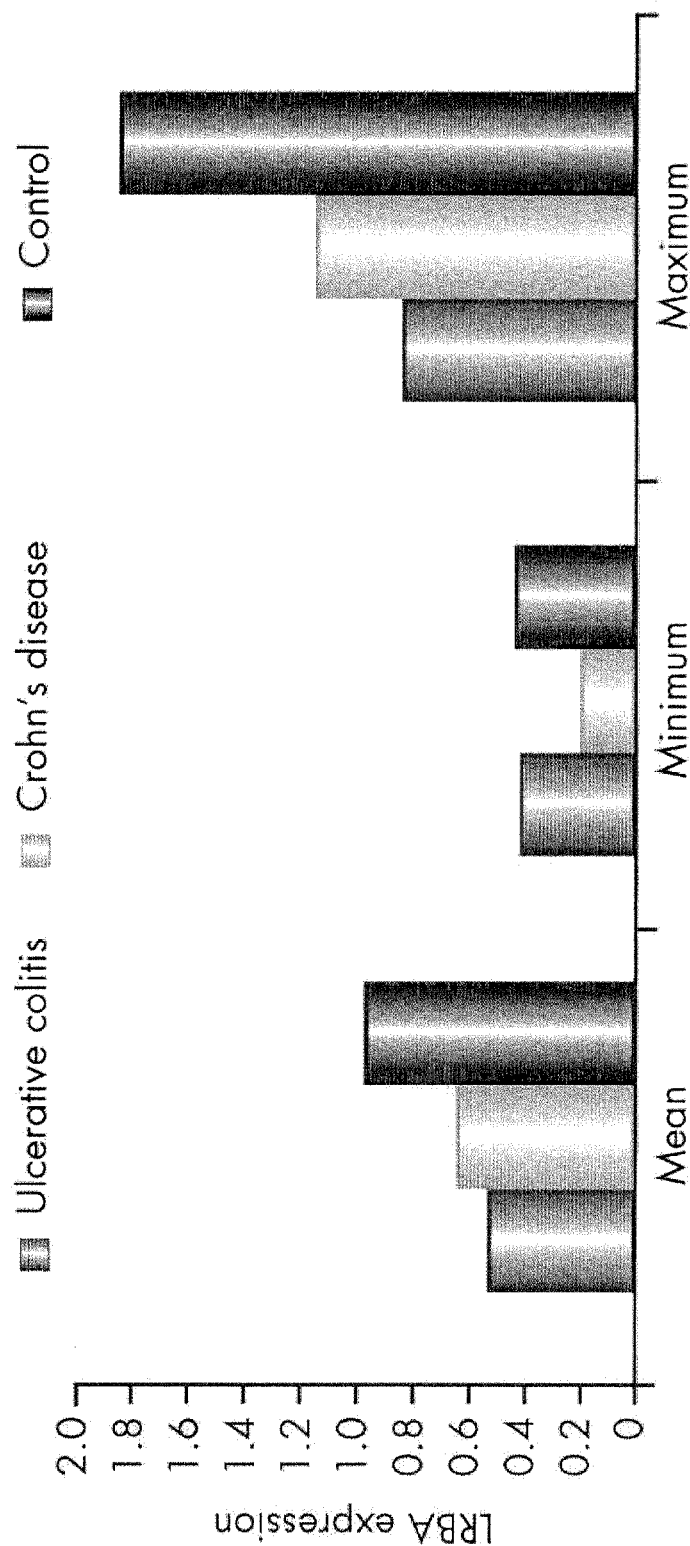
FIG. 5 shows LRBA expression for average real-time PCR quantification of LRBA expression normalized to a housekeeping control gene (18s RNA).

RNA isolated from patient leukocytes was run on a gel, seen in FIG. 3. Real time quantitative PCR was performed on 17 Crohn's, 5 ulcerative colitis and 12 controls. To control for different starting concentrations of total RNA, 18S rRNA, a ubiquitous, transcriptionally stable gene was used to normalize the concentration. Each subject was analyzed by using 2 different concentrations of starting cDNA (10 ng and 0.8 ng) and 3 separate reactions were performed on each. Differences noted were all well within the accepted standard deviation for the test. The normalized 6 reactions were then averaged, seen in FIG. 4. The mean LRBA expression for each subject within the IBD group was compared to the subject's disease activity. The quantitative expression of LRBA ranged from 0.45 to 1.85 in the controls, 0.21 to 1.15 in patients with Crohn's disease, and 0.43 to 0.85 in patients with ulcerative colitis. Mean LRBA expression was 34% lower in the Crohn's disease group and 45% lower in the ulcerative colitis group when compared to controls, seen in FIG. 5.

The ANOVA test was used to identify statistical significant differences amongst the three groups as a whole. The analysis of variance test revealed an F-value of 4.77 with a p-value of 0.0156, indicating that there is a statistical difference between these 3 groups mean LRBA expression. The Tukey test evaluated for specific differences between groups. It identified statistical significance at the 95% confidence levels for both the Crohn's disease and the ulcerative colitis groups when compared to the controls, seen in Table 2. There was no statistical significant difference between the Crohn's and ulcerative colitis group.

TABLE 2

Pair-wise comparison of the means by Tukey test

| Comparison | Difference between means | Simultaneous 95% confidence limits | |  |
|---|---|---|---|---|
| Control vs Crohn's disease | 0.326 | 0.0238 | 0.6281 | * |
| Control vs ulcerative colitis | 0.4403 | 0.0138 | 0.8669 | * |
| Crohn's disease vs ulcerative colitis | 0.1144 | −0.2933 | 0.522 | |

* Indicates statistically significant difference between groups.

Regulation of intestinal inflammation is guided by the innate immune system. Toll-like receptors (TLRs), part of the innate immune system respond to pathogens within the gastrointestinal tract. Dysregulation of this process results in dysfunctional bacterial clearance by leukocytes leading to downstream signaling abnormalities within the intestinal epithelia (De Jager, P. L., et al. The role of the Toll receptor pathway in susceptibility to inflammatory bowel diseases. Genes Immun. 2007 July; 8(5):387-97; Browning, B. L. Has toll-like receptor 4 been prematurely dismissed as an inflammatory bowel disease gene? Association study combined with meta-analysis shows strong evidence for association. Am J Gastroenterol. 2007 November; 102(11):2504-12). This signaling has been shown to be abnormal in Crohn's disease and ulcerative colitis. The TLR pathway not only protects the intestine from pathogens but maintains homeostasis through tolerance and regulation of gut flora (Browning, B. L., et al. Am J Gastroenterol. 2007 November; 102 (11):2504-12; Fukata, M., Abreu, M. T. TLR4 signaling in the intestine in health and disease. Biochem Soc Trans. 2007 December; 35(Pt 6):1473-8; Abreu, M. T., Sparrow, M. P. Translational Research in Inflammatory Bowel Disease. The Mount Sinai Journal of medicine Vol 73 No. 8 Dec. 2006).

TLR4, a pattern recognition receptor, recognizes conserved motifs of gram negative bacteria, specifically lipopolysaccharides. This recognition stimulates signal transduction resulting in activation of the NFkB pathway. This pathway is upregulated in inflammatory bowel disease (De Jager, P. L., et al. Genes Immun. 2007 July; 8(5):387-97; Fukata, M., Abreu, M. T. Biochem Soc Trans. 2007 December; 35(Pt 6):1473-8). Population based studies have shown that mutations in TLR4 result in an increased susceptibility to Crohn's disease. TLR 4 A299G appears to be a significant risk factor for CD, in particular colonic, nonstricturing disease (Hume, G. E. Novel NOD2 haplotype strengthens the association between TLR4 Asp299gly and Crohn's disease in an Australian population. Inflamm Bowel Dis. 2008 May; 14(5):585-90).

Lipopolysaccharide Responsive Beige-like Anchor (LRBA) was identified by using a retroviral gene trapping system using LPS as the trigger (Kerr, W. G., et al. Proc Natl Acad Sci. Vol 93 p. 3947-52). Sequencing LRBA revealed binding sites for NFkB (Wang, W. L., et al. Oncogene. 2004 May 20; 23(23):4089-97), seen in FIG. 6, further supporting the notion of the genes involvement in this pathway. LRBA contains features similar to CHS1/NG genes which have been linked to deficiencies in cell mediated cytolysis by both T cells and NK cells, defective bacteriocidal activity, and chemotaxis by granulocytes and monocytes (Wang, W. L. J Immunol. 2001 Apr. 1; 166(7):4586; Wang, N., et al. BEACH family of proteins phylogenetic and functional analysis of six Dictyostelium BEACH proteins. J Cell Biochem. 2002:86 (3):561-70; Kaplan, J., et al. Chediak-Higashi syndrome. Curr Opin Hematol. 2008 January; 15(1):22-9).

Quantitative real time PCR was performed on LRBA in patients with IBD and compared them to controls. LRBA expression is markedly reduced in IBD patients compared to controls. This data and the presence of multiple NFkB sites in the LRBA promoter indicate LRBA is part of the NFkB signal transduction cascade. Whether it's diminished expression is a result of a breakdown of the innate immune response, more specifically defective TLR4 signaling, has yet to be determined. Underexpression of LRBA drives the production of the other inflammatory molecules in the NFkB pathway thus contributing to the inflammatory environment seen in Crohn's disease and ulcerative colitis. Thus, the underexpression of LRBA serves as a marker of disease and is a therapeutic target.

Patients with mutations in NOD2 are at increased risk of developing fibrostenotic Crohn's disease and some studies associate TLR4 with purely colonic disease (Van Limbergen, J., et al. The genetics of Inflammatory Bowel Disease. The Am J of Gastroenterology 2007; 102:2820-31). A specific phenotypic trend was not identified in the underexpressed LRBA Crohn's patients. The ulcerative colitis group possessed universally down regulated expression. These findings may be secondary to the sample size of the study.

Patients with Crohn's and ulcerative colitis (UC) are at increased risk of developing colon cancer, thought to be due to chronic inflammation (Futaka, M., et al. Toll-like receptor-4 promotes the development of colitis-associated colorectal tumors. Gastroenterology 2007 December; 133(6):1869-81; Komarova, E. A., et al. p53 is a suppressor of inflammatory response in mice FASEB J. 2005; 19:1030-1032). Characterization of the molecular mechanisms linking inflammation and colon carcinogenesis is not fully understood (Narayan, S., Roy, D. Role of APC and DNA mismatch repair genes in the development of colorectal cancers. Molecular Cancer. 2003. Dec. 12; 2:41). TLR4 signaling is critical for colon carcinogenesis in chronic colitis. LRBA is downregulated by P53 and upregulated by E2F, indicating that mutations in tumor suppressors p53 and Rb could contribute to the deregulation of LRBA. The link between inflammation and colitis associated colon cancer likely involves cross-talking between NF-kB and P53 (Karrasch, T., Jobin, C. NF-kB and the intestine: Friend or Foe? Inflamm Bowel Dis. 2008; 14:114-23; Komarova, E. A., et al. p53 is a suppressor of inflammatory response in mice FASEB J. 2005; 19:1030-1032). LRBA is likely involved in the communication between the inflammatory and carcinogenic pathways in colitis associated colon cancer.

The disclosures of all publications cited above are expressly incorporated herein by reference, each in its entirety, to the same extent as if each were incorporated by reference individually.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It is also to be understood that the following claims are intended to cover all of the generic and specific features of the invention herein described, and all statements of the scope of the invention which, as a matter of language, might be said to fall therebetween. Now that the invention has been described,

We claim:

1. A method of detecting a colon disorder in a subject, comprising obtaining a sample comprising peripheral blood mononuclear cells (PBMCs) from the subject, and measuring a level or activity of Lipopolysaccharide Responsive Beige-like Anchor (LRBA) in the PBMCs, wherein a measured LRBA level or activity less than a normal control is indicative of the colon disorder, and wherein the colon disorder comprises inflammatory bowel disease or colon cancer.

2. The method of claim 1, wherein the colon disorder is inflammatory bowel disease.

3. The method of claim 2, wherein the inflammatory bowel disease is Crohn's disease or ulcerative colitis.

4. The method of claim 1, wherein the colon disorder is colon cancer.

SEQUENCE LISTING

```
<160> NUMBER OF SEQ ID NOS: 1

<210> SEQ ID NO 1
<211> LENGTH: 1439
<212> TYPE: DNA
<213> ORGANISM: Homo sapiens

<400> SEQUENCE: 1
cctccgcgcc aagagaccct acggtaactt aacaacagca ggagcgccaa aatccccgcc      60
tcaggacttg gcagaagcac ctcccgaggt ccgagagtgg gagaggggaa agtgtaggcc     120
ctcggacgga agggtctctc ctcgccgggc cgggtacaca cctggtgcta ccagagcagc     180
gcgcctagtg cagccggaag ccccagccca gcactccggc tggctcgggg ccccttggc     240 tgtccgcgcg tcgtcaccgc gcccccgccg cgcggctgcc tccgccttcg cgccctcccg     300
gcccgcgcac tcgcgctcgc gcacgcgcac gccgcgcccg gcagcactcg gcgctgtcat     360
cgcggccggg agcagcttca gtgggcacac gacagccgcg cgacccgtgg cggggcgagc     420
tgtggcagta gcatcctcac cactcgcagc agcctcagcc gcggcgcccg tagcgccagc     480
agcggctgct tttgcaaagg ctgagcgcag gggcggggcg ggccaggaag ccatggagtt     540
ctgtgcagcc gcggactccc ggggagcgga ctagggaaac ttggaggctg cgaccaggtg     600
cactgacctc tctgtcctcc cttctctccc tgcggtggcc gctgggtttc tctggccgct     660
cccctccctt cctgccacca cacacacctc cccaccccett cccgtcgaat ctcaggtgcc     720
tgagagaggt gcttcactcc tcccactggg ccgagcattt agaataatca ccgccccctt     780
cccccgcctt ttcctgccct ggatctccgc cgccacctcg gtctcgctgc tcctgggcgg     840
ggggtgagga cgagtccgga gtatctgggt gaggaagaac tttctacctc tgtgatagct     900
tgtgggcccc ccttctttcc tccgatccct cctttccccg cgacagtttc tctttctagt     960
gcacctgtga ggagaggtta ccctgcgcct agaacctgca cgagagtggg ggaggagtga    1020
gcctgttcgg gggcctcttg gacctgcctt cacccagaac ccagcttttt gagcccggga    1080
gaagcgggtg gctagtagtg gggtgccttt agtaacttac ttgaccgaca ataactattt    1140
ccctcttgtc ccctcaaaac cctaaaacaa aacctagcct atttaacata tatttaatct    1200
tccaataggg tttggcgttg ttgtcagcct cgggagaga gattggacaa atattctcca    1260
agaggaggag ggcgacgcca aggactttcc acatcaactg ctttggggta tctccacaag    1320
ttggaagagg gaccctttcg ttttgcattg cgtgtgttgt gctcattacc agtgcagcga    1380
ctgccgtccc agggtgactc tgagttgtcc tttatcgtga gctagcaatg gctagcgaa     1439
```

5. The method of claim 1, further comprising carrying out one or more confirmatory tests for the colon disorder if the measured LRBA level is less than the normal control.

6. The method of claim 5, wherein the one or more confirmatory tests is selected from the group consisting of a blood test, test for blood in a stool sample, test for a target microorganism in a stool sample, colonoscopy, sigmoidoscopy, X-ray with barium, computerized axial tomography, and capsule tomography, or a combination of two or more of the foregoing.

7. The method of claim 1, wherein the sample is a blood sample.

8. The method of claim 1, wherein said measuring comprises measuring the amount of LRBA messenger RNA in the PBMCs.

9. The method of claim 1, wherein said measuring comprises measuring the amount of LRBA protein in the PBMCs.

10. The method of claim 1, wherein said measuring comprises measuring the activity of LRBA in the PBMCs.

11. The method of claim 8, wherein said measuring comprises contacting the sample with a detectably labeled nucleic acid that is complementary to a portion of LRBA messenger RNA.

12. The method of claim 9, wherein said measuring comprises contacting the sample with a detectably labeled immunological reagent that binds to LRBA protein.

13. A method of detecting inflammatory bowel disease in a subject, comprising obtaining a sample comprising peripheral blood mononuclear cells (PBMCs) from the subject, and measuring Lipopolysaccharide Responsive Beige-like Anchor (LRBA) expression level in the PBMCs, wherein a measured LRBA expression level less than a normal control LRBA expression level is indicative of the inflammatory bowel disease.

14. The method of claim 13, wherein said measuring comprises performing quantitative real-time polymerase chain reaction.

15. The method of claim 13, wherein the inflammatory bowel disease comprises ulcerative colitis.

16. The method of claim 13, wherein the inflammatory bowel disease comprises Crohn's disease.

* * * * *

UNITED STATES PATENT AND TRADEMARK OFFICE
CERTIFICATE OF CORRECTION

PATENT NO. : 8,440,395 B2
APPLICATION NO. : 12/577161
DATED : May 14, 2013
INVENTOR(S) : William G. Kerr and Joseph M. McKinley Page 1 of 1

It is certified that error appears in the above-identified patent and that said Letters Patent is hereby corrected as shown below:

In the Specifications:

Column 5,
Line 9, "do not hind" should be --do not bind--

Signed and Sealed this
Twentieth Day of August, 2013

Teresa Stanek Rea
*Acting Director of the United States Patent and Trademark Office*